(12) United States Patent
Kim et al.

(10) Patent No.: US 11,731,969 B2
(45) Date of Patent: Aug. 22, 2023

(54) CRYSTAL POLYMORPH OF 8-BROMO-2-(1-METHYLPIPERIDIN-4-YLAMINO)-4-(4-PHENOXYPHENYLAMINO) PYRIDO[4,3-D]PYRIMIDIN-5(6H)-ONE HYDROCHLORIDE AND METHOD FOR PREPARING SAME

(71) Applicant: OSCOTEC INC., Seongnam-si (KR)

(72) Inventors: Jung-Ho Kim, Seongnam-si (KR); Jang-Sik Choi, Seongnam-si (KR); Hee Kyu Lee, Seongnam-si (KR); Song-eun Park, Seongnam-si (KR); Dong-Sik Jung, Seongnam-si (KR); Yung-Geun Choi, Seongnam-si (KR); Jong-Sung Koh, Seongnam-si (KR); Se-Won Kim, Seongnam-si (KR); Jaekyoo Lee, Seongnam-si (KR)

(73) Assignee: OSCOTEC INC., Seongnam-si (KR)

( * ) Notice: Subject to any disclaimer, the term of this patent is extended or adjusted under 35 U.S.C. 154(b) by 243 days.

(21) Appl. No.: 17/266,141

(22) PCT Filed: Aug. 12, 2019

(86) PCT No.: PCT/KR2019/010210
§ 371 (c)(1),
(2) Date: Feb. 5, 2021

(87) PCT Pub. No.: WO2020/040467
PCT Pub. Date: Feb. 27, 2020

(65) Prior Publication Data
US 2021/0292322 A1   Sep. 23, 2021

(30) Foreign Application Priority Data
Aug. 23, 2018  (KR) .................. 10-2018-0098681

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .................... C07D 471/04; C07B 2200/13
See application file for complete search history.

(56) References Cited

U.S. PATENT DOCUMENTS

2003/0114470 A1*  6/2003  Wizel ............... A61P 43/00
                                                514/263.38
2013/0274274 A1   10/2013  Kim et al.

FOREIGN PATENT DOCUMENTS

KR   10-2007-0083471 A   8/2007
KR      10-0774271 B1   11/2007
(Continued)

OTHER PUBLICATIONS

Hee Kyu Lee et al., "G-749, a novel FLT3 kinase inhibitor, can overcome drug resistance for the treatment of acute myeloid leukemia", Blood, 2014, vol. 123, No. 14, pp. 2209-2219 (11 pages total).

(Continued)

*Primary Examiner* — Jared Barsky
*Assistant Examiner* — Liyuan Mou
(74) *Attorney, Agent, or Firm* — Sughrue Mion, PLLC (57) ABSTRACT

An embodiment relates to a crystal polymorph of 8-bromo-2-(1-methylpiperidin-4-ylamino)-4-(4-phenoxyphenylamino)pyrido [4,3-d]pyrimidin-5(6H)-one hydrochloride which can effectively suppress FLT3 and has excellent stability even in a high temperature and humid environment, and a method for preparing same.

2 Claims, 5 Drawing Sheets

(56) References Cited

FOREIGN PATENT DOCUMENTS

| KR | 10-2012-0140643 A | 12/2012 |
|----|-------------------|---------|
| KR | 10-2014-0144709 A | 12/2014 |
| KR | 10-2015-0002952 A | 1/2015  |

OTHER PUBLICATIONS

Caira, "Crystalline Polymorphism of Organic Compounds", Topics in Current Chemistry, 1998, vol. 198, pp. 163-208 (46 pages total).
Abdul S.K. Mudalip, et al., "Effects of Solvents on Polymorphism and Shape of Mefenamic Acid Crystals", MUCET 2017, MATEC Web of Conferences, Feb. 23, 2018, pp. 1-7, vol. 150.
International Searching Authority, International Search Report for PCT/KR2019/010210 dated Nov. 25, 2019 (PCT/ISA/210).
Harry G. Brittain, "Polymorphism in Pharmaceutical Solids", Drugs and the Pharmaceutical Sciences, Second Edition, vol. 192 (654 pages), 2009.

\* cited by examiner

CRYSTAL POLYMORPH OF 8-BROMO-2-(1-METHYLPIPERIDIN-4-YLAMINO)-4-(4-PHENOXYPHENYLAMINO)PYRIDO[4,3-D]PYRIMIDIN-5(6H)-ONE HYDROCHLORIDE AND METHOD FOR PREPARING SAME

CROSS REFERENCE TO RELATED APPLICATIONS

This application is a National Stage of International Application No. PCT/KR2019/010210 filed Aug. 12, 2019, claiming priority based on Korean Patent Application No. 10-2018-0098681 filed Aug. 23, 2018.

TECHNICAL FIELD

Embodiments relate to a crystalline polymorph of 8-bromo-2-(1-methylpiperidin-4-ylamino)-4-(4-phenoxyphenylamino)pyrido[4,3-d]pyrimidin-5(6H)-one hydrochloride and a process for preparing the same.

BACKGROUND ART

FLT3 (FMS-like tyrosine kinase 3, also known as Flk2) is one of the class III receptor tyrosine kinase (RTK) and plays an important role in the proliferation and differentiation of hematopoietic stem cells. The active mutation or overexpression of FLT3 is found in acute myeloid leukemia (AML), acute lymphocytic leukemia (ALL), mastocytosis, and gastrointestinal stromal tumors (GIST). Let alone the active mutation, the autocrine or paracrine ligand stimulation of overexpressed FLT3 may also contribute to a malignant phenotype.

Ligands for FLT3 are expressed by bone marrow stromal cells and other cells and cooperate with other growth factors to stimulate the proliferation of stem cells, progenitor cells, dendritic cells, and natural killer cells. FLT3 is associated with myeloproliferative disorders and hematologic malignancies. In addition, FLT3 is expressed in a large part of dendritic cell progenitors, and the stimulation of FLT3 causes proliferation of the progenitor and differentiation into dendritic cells (DC). Since the dendritic cells are a major initiator of T-cell mediated immune responses, including autoimmune responses, the inhibition of FLT3 is a major mechanism for downregulating the dendritic cell-mediated inflammation and autoimmune responses.

Meanwhile, crystalline compounds have a unique crystal pattern. This pattern may be a single crystal form or two or more polymorphic forms. Such polymorphic compounds may show differences in moisture absorption, and their physical properties such as solubility and melting point are also different. Thus, although polymorphic compounds have the same chemical structural formula, there may be differences in stability and physiological activity of the compounds as they have different crystalline forms. In particular, in the case of pharmaceutical use, the crystal forms may have a significant impact on the convenience of preparation of pharmaceutical raw materials, solubility, storage stability, and biopharmacological activity. In addition, according to the guidelines and regulations promulgated by the drug licensing authorities in each country, the stability of drug crystalline forms is required for the approval of drug marketing.

Accordingly, there has been a demand for the development and research of a new crystalline form that can effectively suppress FLT3, has excellent stability even in a high temperature and humid environment, and has improved solubility.

DETAILED DESCRIPTION OF THE INVENTION

Technical Problem

The embodiments aim to provide a crystalline polymorph of 8-bromo-2-(1-methylpiperidin-4-ylamino)-4-(4-phenoxyphenylamino)pyrido [4,3-d]pyrimidin-5(6H)-one hydrochloride, which can effectively suppress FLT3 and has excellent stability even in a high temperature and humid environment, and a process for preparing the same.

Solution to the Problem

The crystalline polymorph (crystalline form (VI)) of 8-bromo-2-(1-methylpiperidin-4-ylamino)-4-(4-phenoxyphenylamino)pyrido [4,3-d]pyrimidin-5(6H)-one hydrochloride according to an embodiment has peaks at diffraction angles (2θ±0.2°) of 5.7°, 8.3°, 8.9°, 15.4°, 16.3°, 17.7°, 18.7°, 21.1°, 22.0°, 24.3°, 25.3°, 26.3°, 28.3°, and 30.8° in the X-ray powder diffraction spectrum using Cu-Kα radiation.

The crystalline polymorph (crystalline form (X)) of 8-bromo-2-(1-methylpiperidin-4-ylamino)-4-(4-phenoxyphenylamino)pyrido [4,3-d]pyrimidin-5(6H)-one hydrochloride according to an embodiment has peaks at diffraction angles (2θ±0.2°) of 7.2°, 12.9°, 14.2°, 18.9°, 19.1°, 21.5°, 26.1°, and 28.9° in the X-ray powder diffraction spectrum using Cu-Kα radiation.

The process for preparing a crystalline polymorph (crystalline form (VI)) of 8-bromo-2-(1-methylpiperidin-4-ylamino)-4-(4-phenoxyphenylamino)pyrido [4,3-d]pyrimidin-5 (6H)-one hydrochloride according to an embodiment comprises suspending 8-bromo-2-(1-methylpiperidin-4-ylamino)-4-(4-phenoxyphenylamino)pyrido [4,3-d]pyrimidin-5(6H)-one hydrochloride in an ethyl acetate solvent.

The process for preparing a crystalline polymorph (crystalline form (VI)) of 8-bromo-2-(1-methylpiperidin-4-ylamino)-4-(4-phenoxyphenylamino)pyrido [4,3-d]pyrimidin-5 (6H)-one hydrochloride according to an embodiment comprises dissolving a compound represented by the following Formula 2 in at least one organic solvent selected from the group consisting of ethanol, methanol, isopropyl alcohol, tetrahydrofuran, and ethyl acetate; and adding hydrochloric acid and isopropyl alcohol to the solution.

[Formula 2]

The process for preparing a crystalline polymorph (crystalline form (VI)) of 8-bromo-2-(1-methylpiperidin-4- ylamino)-4-(4-phenoxyphenylamino)pyrido [4,3-d]pyrimidin-5 (6H)-one hydrochloride according to an embodiment comprises dissolving 8-bromo-2-(1-methylpiperidin-4-ylamino)-4-(4-phenoxyphenylamino)pyrido [4,3-d]pyrimidin-5 (6H)-one hydrochloride in a dimethyl sulfoxide solvent; and adding an antisolvent to the solution.

The process for preparing a crystalline polymorph (crystalline form (X)) of 8-bromo-2-(1-methylpiperidin-4-ylamino)-4-(4-phenoxyphenylamino)pyrido [4,3-d]pyrimidin-5 (6H)-one hydrochloride according to an embodiment comprises dissolving 8-bromo-2-(1-methylpiperidin-4-ylamino)-4-(4-phenoxyphenylamino)pyrido [4,3-d]pyrimidin-5(6H)-one hydrochloride in an ethanol solvent.

Advantageous Effects of the Invention

The crystalline polymorph of 8-bromo-2-(1-methylpiperidin-4-ylamino)-4-(4-phenoxyphenylamino)pyrido[4,3-d]pyrimidin-5(6H)-one hydrochloride according to an embodiment can effectively inhibit FLT3 while it has excellent stability even in a high temperature and humid environment and improved solubility.

The process for preparing a crystalline polymorph of 8-bromo-2-(1-methylpiperidin-4-ylamino)-4-(4-phenoxyphenylamino)pyrido [4,3-d]pyrimidin-5 (6H)-one hydrochloride according to an embodiment has excellent reproducibility.

BEST MODE FOR CARRYING OUT THE INVENTION

Hereinafter, the invention will be described in detail with reference to embodiments. The embodiments are not limited to what is disclosed below. Rather, they may be modified in various forms as long as the gist of the invention is not altered.

In this specification, when a part is referred to as "comprising" an element, it is to be understood that the part may comprise other elements as well, unless otherwise indicated.

All numbers and expressions indicating the amounts of components, reaction conditions, and the like used herein are to be understood as being modified by the term "about" unless otherwise indicated.

8-bromo-2-(1-methylpiperidin-4-ylamino)-4-(4-phenoxyphenylamino)pyrido[4,3-d]pyrimidin-5(6H)-one hydrochloride (Compound 1) represented by the following Formula 1 has an effect of inhibiting the activity of protein kinase (see Korean Laid-open Patent Publication No. 2014-0144709). However, its solubility is low, and its stability under humid conditions is low, making it difficult to be developed as injections and oral preparations.

[Formula 1]

A crystalline polymorph of 8-bromo-2-(1-methylpiperidin-4-ylamino)-4-(4-phenoxyphenylamino)pyrido[4,3-d]pyrimidin-5(6H)-one hydrochloride according to an embodiment has characteristic peaks at diffraction angles (2θ±0.2°) of 5.7°, 8.3°, 8.9°, 15.4°, 16.3°, 17.7°, 18.7°, 21.1°, 22.0°, 24.3°, 25.3°, 26.3°, 28.3°, and 30.8° in the X-ray powder diffraction spectrum using Cu-Kα radiation. The crystalline polymorph of 8-bromo-2-(1-methylpiperidin-4-ylamino)-4-(4-phenoxyphenylamino)pyrido [4,3-d]pyrimidin-5(6H)-one hydrochloride having characteristic peaks at the above diffraction angles is referred to as a crystalline form (VI).

According to an embodiment, the crystalline form (VI) may show a peak in the range of 150° C. to 300° C. when analyzed with a differential scanning calorimeter (DSC). For example, it may be 150° C. to 290° C., 170° C. to 300° C., 180° C. to 300° C., 200° C. to 300° C., 220° C. to 300° C., 240° C. to 300° C., 220° C. to 280° C., 240° C. to 280° C., or 250° C. To 280° C., but it is not limited thereto.

A crystalline polymorph of 8-bromo-2-(1-methylpiperidin-4-ylamino)-4-(4-phenoxyphenylamino)pyrido[4,3-d]pyrimidin-5(6H)-one hydrochloride according to an embodiment has characteristic peaks at diffraction angles (2θ±0.2°) of 7.2°, 12.9°, 14.2°, 18.9°, 19.1°, 21.5°, 26.1°, and 28.9° in the X-ray powder diffraction spectrum using Cu-Kα radiation. The crystalline polymorph of 8-bromo-2-(1-methylpiperidin-4-ylamino) (4-phenoxyphenylamino) pyrido [4,3-d]pyrimidin-5(6H)-one hydrochloride having characteristic peaks at the above diffraction angles is referred to as a crystalline form (X).

According to an embodiment, the crystalline form (X) may show a peak in the range of 150° C. to 300° C. when analyzed with a differential scanning calorimeter (DSC). For example, it may be 170° C. to 300° C., 180° C. to 300° C., 180° C. to 280° C., 180° C. to 260° C., 180° C. to 240° C., 200° C. to 300° C., 200° C. to 280° C., 200° C. to 260° C., 200° C. to 240° C., or 200° C. to 220° C., but it is not limited thereto.

The process for preparing a crystalline form (VI) according to an embodiment comprises suspending 8-bromo-2-(1-methylpiperidin-4-ylamino)-4-(4-phenoxyphenylamino)pyrido[4,3-d]pyrimidin-5(6H)-one hydrochloride in an ethyl acetate solvent.

According to an embodiment, the process for preparing a crystalline form (VI) may further comprise stirring the suspension for 15 to 25 hours at room temperature (25° C.).

For example, it may be stirred for 15 to 20 hours or 20 to 25 hours, but it is not limited thereto.

According to an embodiment, the process for preparing a crystalline form (VI) may further comprise drying the suspension at room temperature (25° C.). In the drying step, the residual solvent may be removed.

According to an embodiment, the process for preparing a crystalline form (VI) may further comprise vacuum drying the suspension from which the residual solvent has been removed for 15 to 25 hours in a temperature range of 40° C. to 70° C. For example, it may be dried under a vacuum in a temperature range of 40° C. to 60° C. or 50° C. to 60° C., but it is not limited thereto.

The process for preparing a crystalline form (VI) according to an embodiment comprises dissolving a compound represented by the following Formula 2 in at least one organic solvent selected from the group consisting of ethanol, methanol, isopropyl alcohol, tetrahydrofuran, and ethyl acetate; and adding hydrochloric acid and isopropyl alcohol to the solution.

[Formula 2]

According to an embodiment, the crystalline form (VI) may be prepared using ethanol as an organic solvent.

According to an embodiment, the process for preparing a crystalline form (VI) may further comprise stirring the solution for 3 to 7 hours in a temperature range of 50° C. to 100° C. For example, it may be stirred in a temperature range of 70° C. to 100° C. or 70° C. to 80° C., but it is not limited thereto.

Thereafter, the process may further comprise lowering the solution to a temperature range of 10° C. to 40° C. and stirring it for 7 to 15 hours to precipitate a solid. For example, it may be lowered to a temperature range of 10° C. to 30° C. or 15° C. to 30° C., but it is not limited thereto.

Thereafter, the process may further comprise vacuum drying the precipitated solid at 50° C. to 100° C. for 15 to 25 hours. For example, it may be dried under a vacuum in a temperature range of 70° C. to 100° C. or 70° C. to 80° C., but it is not limited thereto.

The process for preparing a crystalline form (VI) according to an embodiment comprises dissolving 8-bromo-2-(1-methylpiperidin-4-ylamino)-4-(4-phenoxyphenylamino) pyrido[4,3-d]pyrimidin-5(6H)-one hydrochloride in a dimethyl sulfoxide solvent; and adding an antisolvent to the solution.

The antisolvent is to precipitate a dissolved solute, which may be one or more selected from the group consisting of methyl isobutyl ketone (MIBK), ethyl acetate, isopropyl acetate, methylene chloride, toluene, tetrahydrofuran, isopropyl alcohol, acetonitrile, 2-methyltetrahydrofuran, acetone, 1-butanol, and methyl ethyl ketone (MEK).

According to an embodiment, the crystalline form (VI) may be prepared using dimethyl sulfoxide as a solvent.

According to an embodiment, the crystalline form (VI) may be prepared using acetonitrile as an antisolvent.

According to an embodiment, the crystalline form (VI) may be prepared using isopropyl acetate as an antisolvent.

According to an embodiment, the crystalline form (VI) may be prepared using 2-methyltetrahydrofuran as an antisolvent.

According to an embodiment, the crystalline form (VI) may be prepared using toluene as an antisolvent.

According to an embodiment, the crystalline form (VI) may be prepared using acetone as an antisolvent.

According to an embodiment, the crystalline form (VI) may be prepared using methyl ethyl ketone (MEK) as an antisolvent.

According to an embodiment, the crystalline form (VI) may be prepared using methyl isobutyl ketone (MIBK) as an antisolvent.

According to an embodiment, the crystalline form (VI) may be prepared using ethyl acetate as an antisolvent.

According to an embodiment, the crystalline form (VI) may be prepared using dimethyl sulfoxide as a solvent and acetonitrile as an antisolvent.

According to an embodiment, the crystalline form (VI) may be prepared using dimethyl sulfoxide as a solvent and isopropyl acetate as an antisolvent.

According to an embodiment, the crystalline form (VI) may be prepared using dimethyl sulfoxide as a solvent and 2-methyltetrahydrofuran as an antisolvent. According to an embodiment, the crystalline form (VI) may be prepared using dimethyl sulfoxide as a solvent and toluene as an antisolvent.

According to an embodiment, the crystalline form (VI) may be prepared using dimethyl sulfoxide as a solvent and acetone as an antisolvent.

According to an embodiment, the crystalline form (VI) may be prepared using dimethyl sulfoxide as a solvent and methyl ethyl ketone (MEK) as an antisolvent.

According to an embodiment, the crystalline form (VI) may be prepared using dimethyl sulfoxide as a solvent and methyl isobutyl ketone (MIBK) as an antisolvent.

According to an embodiment, the crystalline form (VI) may be prepared using dimethyl sulfoxide as a solvent and ethyl acetate as an antisolvent.

According to an embodiment, the process for preparing a crystalline form (VI) may further comprise filtering the solid precipitated by the antisolvent and then vacuum drying it at 40° C. to 60° C. for 15 to 25 hours. For example, it may be dried under a vacuum in a temperature range of 40° C. to 60° C. or 50° C. to 60° C., but it is not limited thereto.

The process for preparing a crystalline form (X) according to an embodiment comprises dissolving 8-bromo-2-(1-methylpiperidin-4-ylamino)-4-(4-phenoxyphenylamino) pyrido[4,3-d]pyrimidin-5(6H)-one hydrochloride in an ethanol solvent.

According to an embodiment, the process for preparing a crystalline form (X) may further comprise heating and refluxing the solution in a temperature range of 50° C. to 100° C. For example, it may be refluxed under heating in a temperature range of 70° C. to 100° C. or 70° C. to 80° C., but it is not limited thereto.

Thereafter, the process may further comprise lowering the solution to a temperature range of 20° C. to 40° C. to precipitate a solid; filtering the precipitated solid, and then vacuum drying it for 30 to 40 hours in a temperature range of 100° C. to 140° C. For example, the solution may be lowered to a temperature range of 20° C. to 35° C. or 25° C. to 30° C., and the solid may be dried under a vacuum in a temperature range of 100° C. to 130° C. or 120° C. to 130° C., but they are not limited thereto.

Embodiments for Carrying Out the Invention

The above will be described in more detail by the following examples. However, the following examples are for illustrative purposes only, and the scope of the examples is not limited thereto.

Example

<Example 1> Preparation of a Crystalline Form (VI)

0.1 g of 8-bromo-2-(1-methylpiperidin-4-ylamino)-4-(4-phenoxyphenylamino)pyrido[4,3-d]pyrimidin-5(6H)-one hydrochloride was added to 3 ml of an ethyl acetate solvent. The solution was stirred at room temperature (25° C.) for 24 hours. It was dried at room temperature to remove the residual solvent, and the solid was then dried under a vacuum at 50° C. for 24 hours to obtain 850 mg of a crystalline form (VI).

Figure 1:
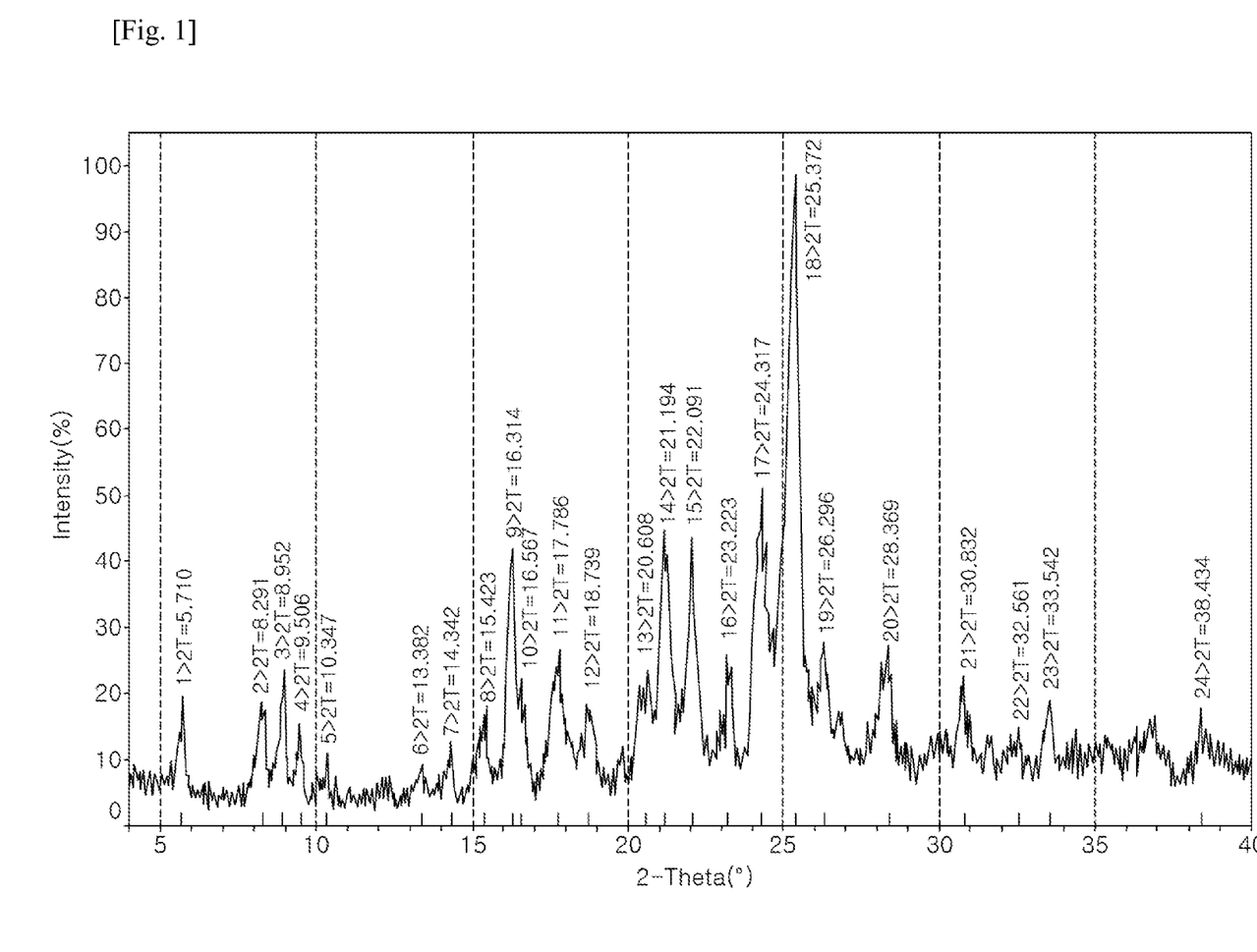
FIG. 1 shows the results of X-ray powder diffraction (XRPD) of a crystalline form (VI).
Figure 2:
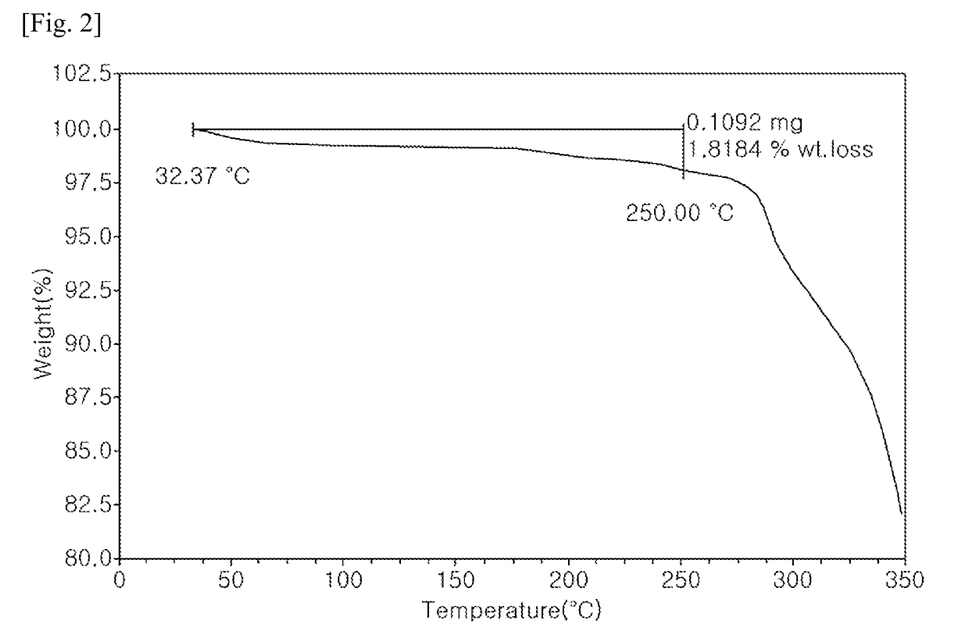
FIG. 2 shows the results of thermogravimetric analysis (TGA) of a crystalline form (VI).
Figure 3:
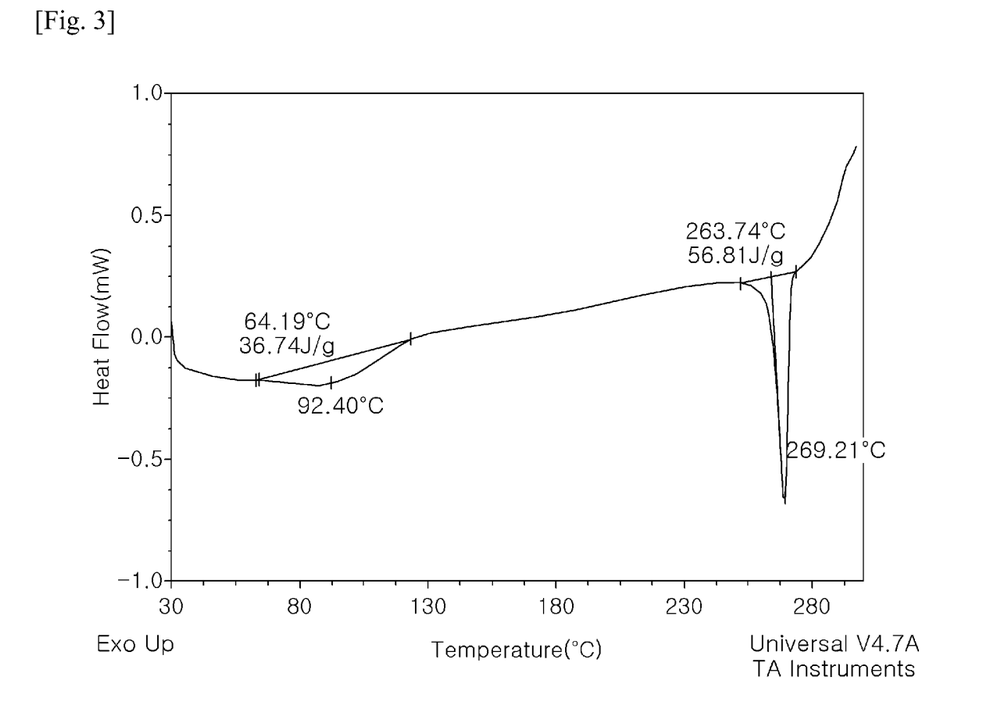
FIG. 3 shows the results of differential scanning calorimetry (DSC) of a crystalline form (VI).

The crystalline form (VI) thus obtained was subjected to X-ray powder diffraction using Cu-Kα radiation, thermogravimetric analysis, and differential scanning calorimetry under the following conditions. The results are shown in FIGS. 1 to 3, respectively. In the differential scanning calorimetry (DSC) of the crystalline form (VI), a peak was observed at 269.21° C. As a result of the thermogravimetric analysis (TGA) of the crystalline form (VI), the weight was reduced by 1.8184%.

*Measurement Conditions for X-Ray Powder Diffraction
Rigaku D/MAX 2200 X-ray powder diffractometer
X-ray Generator: Cu, kα, (λ=1.54056)
Tube voltage: 40 kV, tube current: 40 mA
DivSlit: 1 deg
DivH.L.Slit: 10 mm
SctSlit: 1 deg
RecSlit: 0.15 mm
Monochromator: fixed monochromator
Scanning scope: 4-40 deg
Scanning step: 10 deg/min
*Measurement Conditions for Thermogravimetric Analysis
TA Q5000 IR TGA system
Heat from 30° C. to 300° C. at 10° C./min
*Measurement Conditions for Differential Scanning Calorimetry
TA Q2000 DSC
Heat from 30° C. to 300° C. at 10° C./min <Example 2> Preparation of a Crystalline Form (VI)

2.0 g of 8-bromo-2-(1-methylpiperidin-4-ylamino)-4-(4-phenoxyphenylamino)pyrido[4,3-d]pyrimidin-5(6H)-one was added to 60 ml of an ethanol solvent. To the solution was added 5N hydrochloric acid and 0.75 ml of isopropyl alcohol. It was stirred at 70° C. to 80° C. for 5 hours. The temperature was lowered to 15° C. to 30° C., and it was then stirred for 12 hours. The solid thus formed was filtered and dried under a vacuum at 70° C. to 80° C. for 18 hours to obtain 1.85 g of a crystalline form (VI).

<Example 3> Preparation of a Crystalline Form (X)

764 g of 8-bromo-2-(1-methylpiperidin-4-ylamino)-4-(4-phenoxyphenylamino)pyrido[4,3-d]pyrimidin-5(6H)-one hydrochloride was added to 23 liters of an ethanol solvent. After the temperature was raised to 70° C. to 80° C., it was refluxed under heating for 5 hours. The temperature was then lowered to 25° C. to 30° C., and the solid thus formed was filtered. The solid thus obtained was dried under a vacuum at 120° C. to obtain 625 g of a crystalline form (X).

Figure 4:
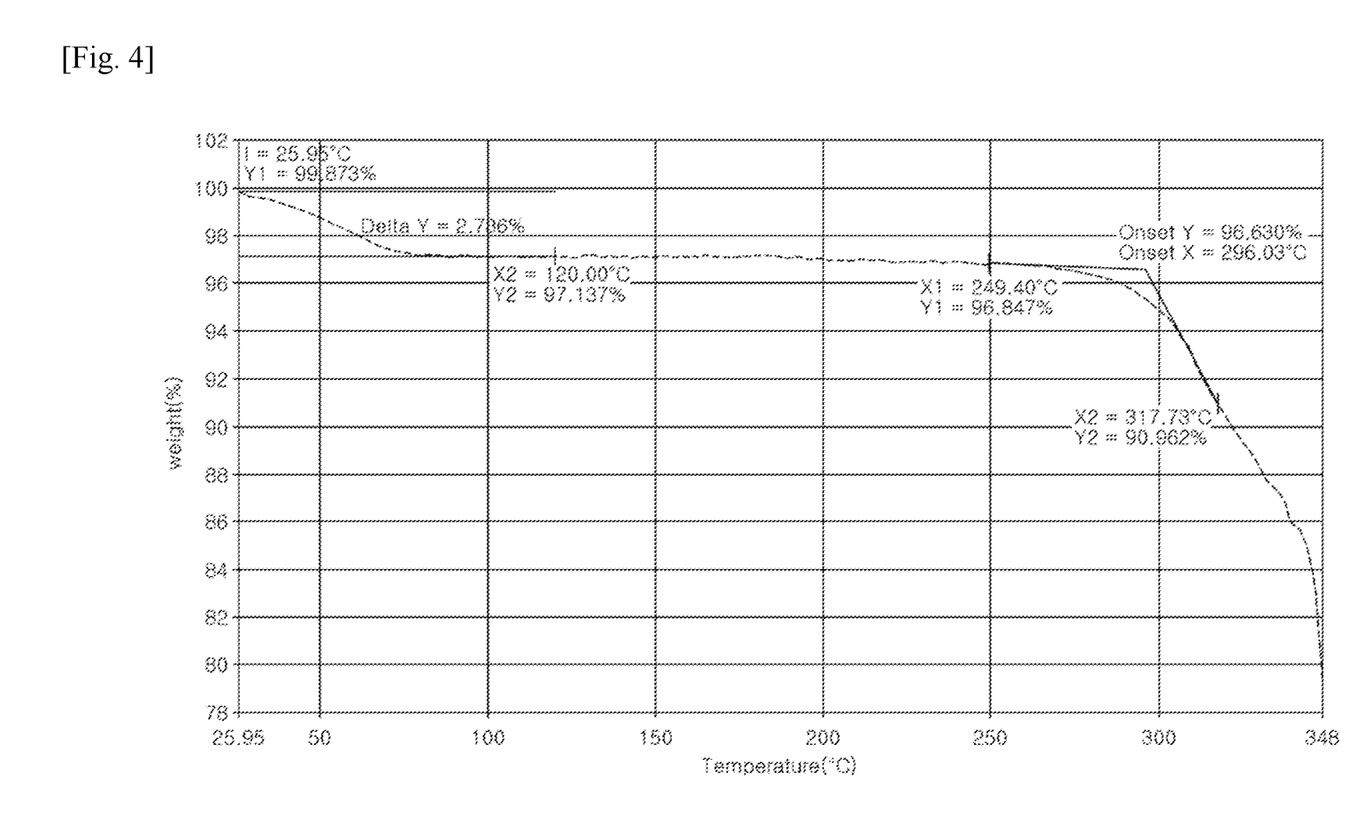
FIG. 4 shows the results of thermogravimetric analysis (TGA) of a crystalline form (X).
Figure 5:
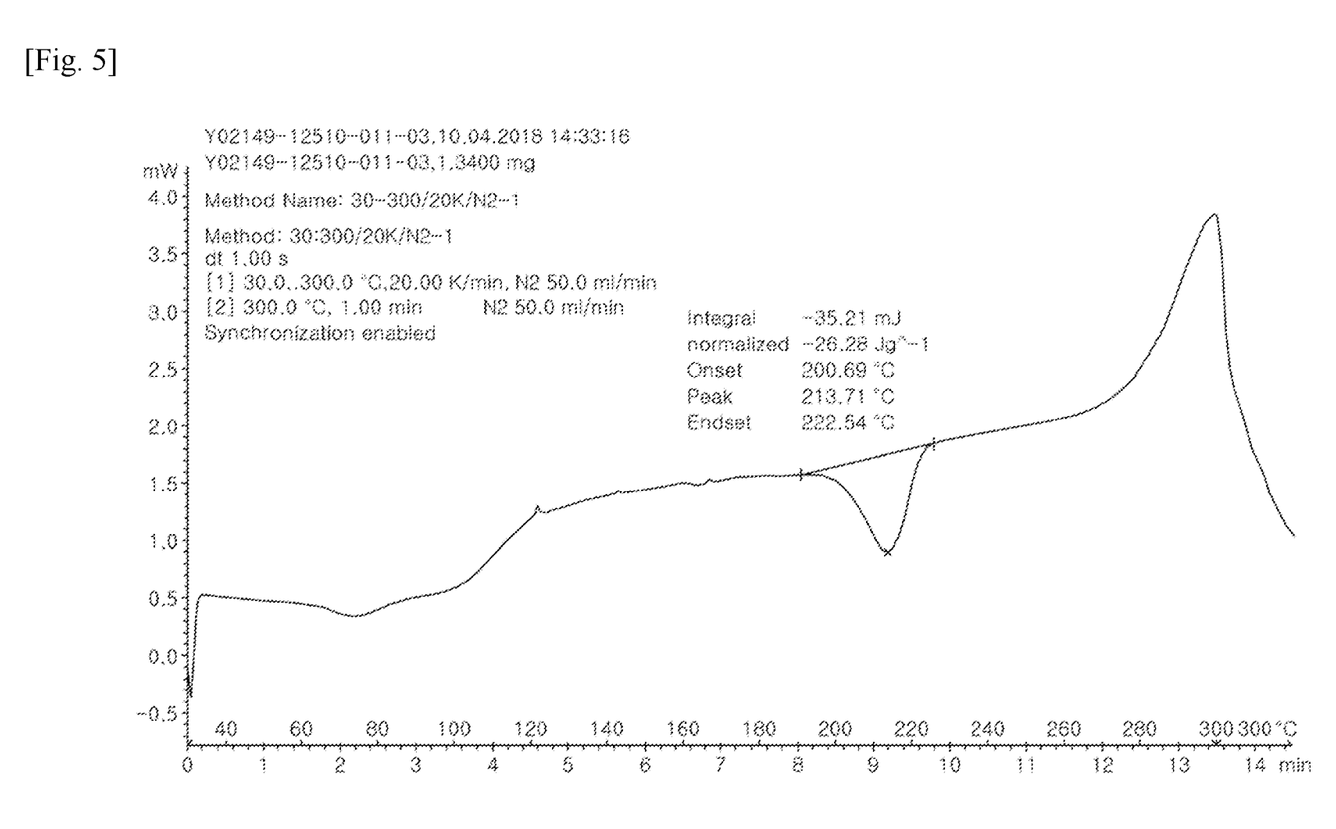
FIG. 5 shows the results of differential scanning calorimetry (DSC) of a crystalline form (X).
Figure 6:
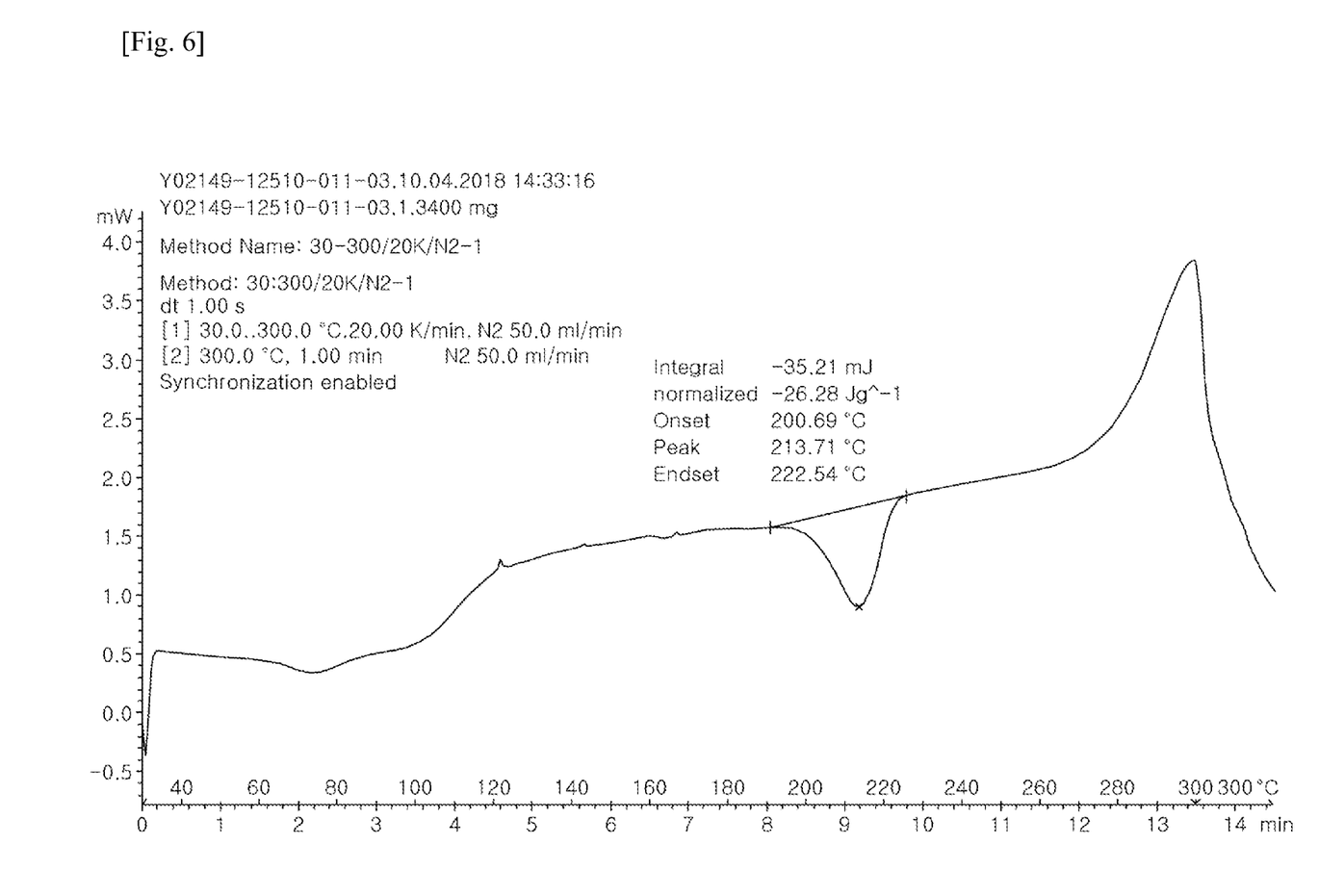

The crystalline form (X) thus obtained was subjected to X-ray powder diffraction using Cu-Kα radiation, thermogravimetric analysis, and differential scanning calorimetry under the same conditions as in Example 1. The results are shown in FIGS. 4 and 5, respectively. In the differential scanning calorimetry (DSC) of the crystalline form (X), a peak was observed at 213.71° C. As a result of the thermogravimetric analysis (TGA) of the crystalline form (X), the weight was reduced by 2.736%.

<Example 4> Preparation of a Crystalline Form (VI)

0.1 g of 8-bromo-2-(1-methylpiperidin-4-ylamino)-4-(4-phenoxyphenylamino)pyrido [4,3-d]pyrimidin-5(6H)-one hydrochloride was added to 5 ml of an N-dimethyl sulfoxide solvent and dissolved at 50° C. The temperature was lowered to 25° C., and 10 ml of acetonitrile as an antisolvent was added to precipitate a solid. The solid was filtered and then dried under a vacuum at 50° C. for 24 hours to obtain 720 mg of a crystalline form (VI).

<Example 5> Preparation of a Crystalline Form (VI)

840 mg of a crystalline form (VI) was obtained in the same experiment as in Example 4, except that isopropyl acetate was used as an antisolvent.

<Example 6> Preparation of a Crystalline Form (VI)

800 mg of a crystalline form (VI) was obtained in the same experiment as in Example 4, except that 2-methyltetrahydrofuran was used as an antisolvent.

<Example 7> Preparation of a Crystalline Form (VI)

910 mg of a crystalline form (VI) was obtained in the same experiment as in Example 4, except that toluene was used as an antisolvent.

<Example 8> Preparation of a Crystalline Form (VI)

850 mg of a crystalline form (VI) was obtained in the same experiment as in Example 4, except that acetone was used as an antisolvent.

<Example 9> Preparation of a Crystalline Form (VI)

910 mg of a crystalline form (VI) was obtained in the same experiment as in Example 4, except that methyl ethyl ketone (MEK) was used as an antisolvent.

<Example 10> Preparation of a Crystalline Form (VI)

890 mg of a crystalline form (VI) was obtained in the same experiment as in Example 4, except that methyl isobutyl ketone (MIBK) was used as an antisolvent.

<Example 11> Preparation of a Crystalline Form (VI)

780 mg of a crystalline form (VI) was obtained in the same experiment as in Example 4, except that ethyl acetate was used as an antisolvent.

<Evaluation Example 1> Evaluation of Solubility

Distilled water was added to 8-bromo-2-(1-methylpiperidin-4-ylamino)-4-(4-phenoxyphenylamino)pyrido[4,3-d]pyrimidin-5(6H)-one hydrochloride (Compound 1) represented by the above Formula 1 and the crystalline form (VI) and the crystalline form (X) obtained in the Examples such that the concentration was 20 mg/ml, which was stirred for 2 hours at room temperature (25° C.) and then filtered. Thereafter, it was diluted 200 times with acetonitrile of a concentration of 50%. The results of the analysis by HPLC (high performance liquid chromatography) are shown in Table 1 below.

TABLE 1

|  | Solubility (mg/ml) | Times |
|---|---|---|
| Compound 1 | 0.25 | — |
| Crystalline form (VI) | 19.1 | 77.2 |
| Crystalline form (X) | 17.3 | 69.2 |

As shown in Table 1 above, the crystalline form (VI) and the crystalline form (X) had improved solubility as compared with Compound 1.

<Evaluation Example 2> Evaluation of Hygroscopicity 8-bromo-2-(1-methylpiperidin-4-ylamino)-4-(4-phenoxyphenylamino)pyrido[4,3-d]pyrimidin-5(6H)-one hydrochloride (Compound 1) represented by the above Formula 1 and the crystalline form (VI) obtained in the Examples were measured for hygroscopicity in a relative humidity range of 0% to 90% at 25° C. using a dynamic moisture adsorption analyzer (DVS). The results are shown in Table 2 below.

TABLE 2

| Relative humidity (%) | Hygroscopicity (%) | |
|---|---|---|
|  | Compound 1 | Crystalline form (VI) |
| 0.0 | 0.001 | 0.004 |
| 10.0 | 0.655 | 0.707 |
| 20.0 | 1.202 | 0.948 |
| 30.0 | 1.695 | 1.132 |
| 40.0 | 2.081 | 1.280 |
| 50.0 | 2.457 | 1.419 |
| 60.0 | 2.823 | 1.561 |
| 70.0 | 3.215 | 1.726 |
| 80.0 | 3.696 | 1.973 |
| 90.0 | 4.584 | 2.452 |

As shown in Table 2 above, the crystalline form (VI) had improved hygroscopicity as compared with Compound 1.

The invention claimed is:

1. A crystalline form of 8-bromo-2-(1-methylpiperidin-4-ylamino)-4-(4-phenoxyphenylamino)pyrido[4,3-d]pyrimidin-5(6H)-one hydrochloride, which has peaks at diffraction angles (2θ±0.2°) of 5.7°, 8.3°, 8.9°, 15.4°, 16.3°, 17.8°, 18.7°, 21.2°, 22.1°, 24.3°, 25.4°, 26.3°, 28.4°, and 30.8° in the X-ray powder diffraction spectrum using Cu-Kα radiation.

2. A process for preparing the crystalline form of 8-bromo-2-(1-methylpiperidin-4-ylamino)-4-(4-phenoxyphenylamino)pyrido[4,3-d]pyrimidin-5(6H)-one hydrochloride of claim 1, which comprises dissolving a compound represented by the following Formula 2 in at least one organic solvent selected from the group consisting of ethanol, methanol, isopropyl alcohol, tetrahydrofuran, and ethyl acetate; and adding hydrochloric acid and isopropyl alcohol to the solution,

[Formula 2]

* * * * *